United States Patent [19]
Collin

[11] Patent Number: 5,344,658
[45] Date of Patent: Sep. 6, 1994

[54] PROCESS AND COMPOSITION USING ONDANSETRON

[75] Inventor: David T. Collin, Ware, England

[73] Assignee: Glaxo Group Limited, London, England

[21] Appl. No.: 5,736

[22] Filed: Jan. 19, 1993

Related U.S. Application Data

[63] Continuation of Ser. No. 755,736, Sep. 6, 1991, abandoned, which is a continuation of Ser. No. 544,644, Jun. 27, 1990, abandoned.

[30] Foreign Application Priority Data

Jun. 28, 1989 [GB] United Kingdom ............... 89148043

[51] Int. Cl.$^5$ ............................................. A61K 9/14
[52] U.S. Cl. ................................... 424/489; 424/484; 424/464; 424/465
[58] Field of Search ................ 424/484, 464, 465, 489

[56] References Cited

PUBLICATIONS

Sekiguchi et al., Chem. Pharm. Bull., 16(12), 2495–2502, 1968.
Pikal et al., Chemical Abstracts, 100:144884x, 1984.
Shirotani et al., Chemical Abstracts, 96:57633v, 1982.

*Primary Examiner*—Paul R. Michl
*Assistant Examiner*—James M. Spear
*Attorney, Agent, or Firm*—Bacon & Thomas

[57] ABSTRACT

The invention relates to a process for reducing the crystal size of ondansetron hydrochloride dihydrate produced by crystallisation from solvent to a size which is suitable for effective distribution in a tablet blend, in particular 100% less that 250 μm. The ondansetron hydrochloride dihydrate is desolvated by drying at elevated temperature and reduced or atmospheric pressure and is then rehydrated.

10 Claims, No Drawings

PROCESS AND COMPOSITION USING ONDANSETRON

This application is a continuation of application Ser. No. 07/755,736, filed Sep. 6, 1991 now abandoned, which is a continuation of application Ser. No. 07/544,644, filed Jun. 27, 1990, now abandoned.

This invention relates to a process for reducing the crystal size of ondansetron hydrochloride dihydrate. More particularly the process involves desolvation and resolvation.

Reduction of crystal size through solvation and desolvation has been described previously, for instance for the compound griseofulvin (K. Sekiguchi et al., Chem. Pharm. Bull., 1968, 16, 2495–2502). Various techniques may be employed to effect desolvation such as drying at an elevated temperature and under vacuum, drying at an elevated temperature and at atmospheric pressure, drying at ambient temperature under a high vacuum, freeze-drying, or drying over a desiccant. However, the precise conditions of desolvation considerably affect the efficiency of the reduction in crystal size.

Ondansetron, the approved name for 1,2,3,9-tetrahydro-9-methyl-3-[(2-methyl-1H-imidazol-1-yl)methyl]-4H-carbazol-4-one, is a highly selective and potent antagonist of 5-hydroxytryptamine (5-HT) at $5\text{-HT}_3$ recaptots. Ondansetron, together with its physiologically acceptable salts and solvetea, is described and claimed in British Patent No. 2153821B, and may be used in the treatment of a variety of conditions, including the nausea and vomiting induced by cancer chemotherapy and radiotherapy (as described, for example, in European Patent Specification No. 226266A).

The preferred form of ondansetron for pharmaceutical formulation is the hydrochloride dihydrate- Ondansetron hydrochloride dihydrate may be presented in a variety of formulations, one of which is as tablets for oral administration, when particularly suitable unit doses of the drug substance for the treatment of emesis are 5 mg and 10 mg.

In the tablet manufacturing process, ondansetron hydrochloride dihydrate is blended with suitable excipients, and the blend is then compressed into tablets.

Since a low dose of drug substance per tablet is required, for example, 5 mg of ondansetron hydrochloride dihydrate in a tablet of 125 mg compression weight, the distribution of the drug substance in the blend is critical in obtaining individual tablets with the correct drug content. Uniform drug distribution in the tablet blend may be achieved using drug substance of appropriate particle size. However, the ondansetron hydrochloride dihydrate obtained by methods described in the art, i.e. that obtained by simple crystallisation from an aqueous solvent mixture with subsequent drying st ambient temperature and pressure contains particles which are too large (i.e. >250 μm) to give an homogeneous distribution of the drug substance in the tablet blend. Indeed if crystalline ondansetron hydrochloride dihydrate produced by such conventional methods were used in tablet manufacture, the tablets so produced would not possess an acceptable drug content which, for a 5 mg tablet, is 5 mg±0.25 mg of ondansetron hydrochloride dihydrate.

Attempts to mill crystals of ondansetron hydrochloride dihydrate to reduce their particle size have proved unsuccessful, for example, comminution milling of ondansetron hydrochloride dihydrate caused screen blockage of coarse and fine screens. Furthermore, although ondansetron hydrochloride dihydrate of particle size <250 μm can be obtained by passing the substance through a 60 mesh sieve (as described, for example, in UK Patent No. 2153821B), this method is not commercially viable.

We have now found e process which reduces the crystal size of ondansetron hydrochloride dihydrate produced by simple crystallisation from solvent (more particularly aqueous solvent mixtures) to a size which is suitable for effective distribution of the drug substance in the tablet blend.

Thus the invention provides a process for reducing the crystal size of ondansetron hydrochloride dihydrate obtained by simple crystallisation from solvent, more particularly an aqueous solvent mixture, to a size which is suitable for effective distribution in a tablet blend, which comprises desolvating the said drug substance by drying at an elevated temperature and reduced or atmospheric pressure, and then rehydrating the ondansetron hydrochloride so formed.

It is possible by means of the process according to the invention to reduce the crystal size of ondansetron hydrochloride dihydrate to the extent that the entire drug substance consists of particles of a sufficiently small size (i.e. less than 250 μm, of which typically about 80% by weight ere less than 63 μm) to give an homogeneous distribution of the drug substance in the tablet blend.

Preferably, the ondansetron hydrochloride dihydrate obtained by crystallisation is desolvated by heating at a temperature greater then 40° C. (e.g. 50° C.) and at reduced pressure (e.g. 200 tort or less) for more than 8 hours. Alternatively, the ondansetron hydrochloride dihydrate obtained by crystallisation may be desolvated at ambient pressure by heating at a temperature of 50° C. or above (more preferably 100° C.).

Most preferably, ondansetron hydrochloride dihydrate obtained by crystallisation is desolvated by heating at 50° C. at a pressure of 100 tort for 24 hours.

The desolvation process may be carried out with or without mechanical agitation.

The resultant ondansetron hydrochloride of reduced crystal size is then rehydrated, for example, by placing it in a humidified atmosphere of, for example, air or nitrogen, at ambient temperature. Rehydration will generally be continued until there is no further gain in weight.

According to another aspect, the invention provides crystalline ondansetron hydrochloride dehydrate characterised in that 100% of the crystals have a size of less than 250μm and at least 80% by weight of the crystals have a crystal size of less than 63 μm (as measured by air-jet sieve analysis).

According to a yet further aspect, the invention provides a pharmaceutical composition in the form of tablets containing crystalline ondansetron hydrochloride dihydrate as active ingredient characterised in that 100% of the ondansetron hydrochloride dihydrate crystals have a size less than 250 μm and at least 80% by weight of the crystals have a crystal size of less than 63 μm (as measured by air-jet sieve analysis). Generally the composition will contain at least one physiologically acceptable carrier or excipient.

The invention is illustrated by the following examples. Temperatures are in ° C. Crystal size was measured by air-jet sieve analysis.

EXAMPLE 1

1,2,3,9-Tetrahydro-9-methyl-3-[(2-methyl-1H-imidazol-1-yl)methyl]-4H-carbazol-4-one hydrochloride dihydrate wherein the crystals are less than 250 μm A solution of 1,2,3,9-tetrahydro-9-methyl-3-[(2-methyl-1H-imidezol-1-yl)methyl]-4H-carbazol-4-one (147 g) in a mixture of isopropanol (670 ml), water (250 ml) and glacial acetic acid (76 ml) at ca. 60° was clarified by filtration and diluted with more water (61 ml) and isopropanol (650 ml). The solution was treated at 70° with 36%w/w hydrochloric acid (46 ml) and cooled to ca. 5°. The resulting suspension was filtered and the filtered solid was washed by displacement with isopropanol (600 ml) to give a solvent wet solid (269 g). A portion of this solid (91 g) was dried at ca. 50° and 200 torr for ca. 16h to give a solid (55 g).

A portion of the dried solid (26 g) was placed in a current of humidified air at ambient temperature until there was no further gain in weight and the title compound (29 g) was obtained.

Particle Size Distribution of Title Compound

| Size (μm) | Cumulative % Undersize (by weight) |
| --- | --- |
| 45 | 43.4 |
| 63 | 83.7 |
| 90 | 97.6 |
| 125 | 98.4 |
| 180 | 99.6 |
| 250 | 100.0 |

EXAMPLE 2

1,2,3,9-Tetrahydro-9-methyl-3-[(2-methyl-1H-imidazol-1-yl)methyl]-4H-carbazol-4-one hydrochloride dihydrate wherein the crystals are less than 250 μm The previous preparation was repeated except that after collection by filtration the solid was dried at ambient temperature and pressure to give large crystals (>45% by weight of crystals larger than 250 μm) of 1,2,3,9-tetrahydro-9-methyl-3-[(2-methyl-1H-imidazol-1-yl)methyl]-4H-carbazol-4-one hydrochloride dihydrate.

Particle Size Distribution of "Large Crystals"

| Size (μm) | Cumulative % Undersize (by weight) |
| --- | --- |
| 45 | 5.8 |
| 63 | 9.8 |
| 90 | 20.8 |
| 125 | 26.7 |
| 180 | 37.8 |
| 250 | 50.6 |
| 355 | 71.5 |
| 500 | 90.9 |
| 710 | 98.4 |
| 1000 | 98.6 |

A sample of this solid (26.9 g) was dried at ambient pressure and 100° for ca. 17 h during which period the weight of the sample was reduced to 24.3 g. The sample was then exposed to ambient temperatures and humidities until it had regained its original weight to afford the title compound.

Particle Size Distribution of Title Compound

| Size (μm) | Cumulative % Undersize (by weight) |
| --- | --- |
| 45 | 47.6 |
| 63 | 94.8 |
| 90 | 100.0 |

EXAMPLE 3

1,2,3,9-Tetrahydro-9-methyl-3-[(2-methyl-1H-imidazol-1-yl)methyl]-4H-carbazol-4-one hydrochloride dehydrate wherein the crystals are less than 250 μm 1,2,3,9-Tetrahydro-9-methyl-3-[(2-methyl-1H-imidazol-1-yl)methyl]-4H-carbazol-4-one hydrochloride dihydrate obtained by crystallisation from a solvent was dried at 52° and 100 torr for 24 h and then rehydrated to give the title compound.

Particle Size Distribution of Title Compound

| Size (μm) | Cumulative % Undersize (by weight) |
| --- | --- |
| 45 | 44.3 |
| 63 | 83.2 |
| 90 | 97.0 |
| 125 | 98.8 |
| 180 | 99.8 |
| 250 | 100.0 |

EXAMPLE 4

1,2,3,9-Tetrahydro-9-methyl-3-[(2-methyl-1H-imidazol-1-yl)methyl]-4H-carbazol-4-one hydrochloride dihydrate wherein the crystals are less than 90 μm 1,2,3,9-Tetrahydro-9-methyl-3-[(2-methyl-1H-imidazol-1-yl)methyl]-4H-carbazol-4-one hydrochloride dihydrate obtained by crystallisation from a solvent was dried at 48° and 100 torr for 24 h and then rehydrated to give the title compound.

Particle Size Distribution of Title Compound

| Size (μm) | Cumulative % Undersize |
| --- | --- |
| 45 | 49.0 |
| 63 | 92.4 |
| 90 | 100.0 |

I claim:

1. A process for reducing the crystal size of ondansetron hydrochloride dihydrate produced by crystallisation from solvent, in which said ondansetron hydrochloride dihydrate is desolvated by drying at elevated temperature and reduced or atmospheric pressure and is then rehydrated, wherein the resulting crystals are suitable for homogeneous distribution in a tablet blend, and wherein 100% of the resulting crystals have a size of less than 250 μm and at least about 80% by weight of the crystals have a size of less than 63 μm.

2. A process according to claim 1, in which said ondansetron hydrochloride dihydrate is prepared by crystallisation from an aqueous solvent mixture.

3. A process according to claim 1, in which said ondansetron hydrochloride dihydrate is desolvated by heating at a temperature greater than 40° C. and at reduced pressure for more than 8 hours.

4. A process according to claim 3, in which said ondansetron hydrochloride dihydrate is desolvated by heating at a temperature of about 50° C. at a pressure of about 100 torr for about 24 hours.

5. A process according to claim 1, in which said ondansetron hydrochloride dihydrate is desolvated by heating at a temperature of 50° C. or above at ambient pressure.

6. A process according to claim 5, in which said temperature is about 100° C.

7. A process according to claim 1, in which said ondansetron hydrochloride dihydrate is rehydrated in a humidified atmosphere at ambient temperature.

8. Crystalline ondansetron hydrochloride dihydrate in which 100% of the crystals have a size of less than 250 μm and at least about 80% by weight of the crystals have a size of less than 63 μm.

9. A pharmaceutical composition in the form of tablets containing crystalline ondansetron hydrochloride dihydrate as active ingredient, in which 100% of said ondansetron hydrochloride dihydrate crystals have a size less than 250 μm and at least about 80% by weight of said crystals have a size less than 63 μm.

10. A pharmaceutical composition according to claim 9, in which each tablet has a nominal content of active ingredient which is 5 mg or 10 mg.

* * * * *